United States Patent [19]

Wang

[11] Patent Number: 5,688,944
[45] Date of Patent: Nov. 18, 1997

[54] CARBAMAZEPINE DERIVATIVES

[75] Inventor: Chengrong Wang, Hockessin, Del.

[73] Assignee: Dade International Inc., Deerfield, Ill.

[21] Appl. No.: 473,810

[22] Filed: Jun. 7, 1995

[51] Int. Cl.⁶ ...................... C07D 223/22; G01N 33/546
[52] U.S. Cl. .......................... 540/529; 540/522; 540/531
[58] Field of Search ................................... 540/522, 529, 540/531

[56]  References Cited

U.S. PATENT DOCUMENTS

| | | |
|---|---|---|
| 2,948,718 | 8/1960 | Schindler . |
| 3,221,011 | 11/1965 | Renz et al. . |
| 4,058,511 | 11/1977 | Singh . |
| 4,401,765 | 8/1983 | Craig et al. . |
| 4,480,042 | 10/1984 | Craig et al. . |
| 4,954,638 | 9/1990 | Young et al. . |

FOREIGN PATENT DOCUMENTS

| | | |
|---|---|---|
| 0 583 820 A1 | 2/1994 | European Pat. Off. . |
| 0 584 854 A1 | 2/1994 | European Pat. Off. . |
| 3417413 A1 | 11/1985 | Germany . |

OTHER PUBLICATIONS

Wang et al, Chemical Abstracts 98:2496, "Reagents and method for determining ligands in a sample of biological liquids", 1983.

*Primary Examiner*—Nathan M. Nutter
*Attorney, Agent, or Firm*—Lois K. Winston

[57]  ABSTRACT

The present invention provides a novel carbamazepine hydrazide compound suitable for covalent attachment to a polymer particle reagent, having the general formula

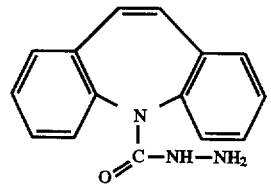

The present invention also provides a novel carbamazepine acid compound suitable for attachment to proteins for the production of carbamazepine immunogens. The carbamazepine antigen of the present invention has the following general structure:

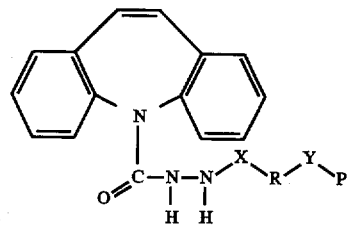

where X is C=O, $CH_2$ or $SO_2$; Y is C=O, $CH_2$, $SO_2$; R is an alkyl and P is a protein or a hapten.

1 Claim, No Drawings

CARBAMAZEPINE DERIVATIVES

BACKGROUND OF THE INVENTION

1. Field of the Invention

The present invention relates to novel carbamazepine compounds for covalent attachment to polymer particle reagents and for use as antigens, including the preparation thereof, and more particularly, to carbamazepine- compounds having nucleophilic characteristics.

2. Description of the Invention Background

Carbamazepine,

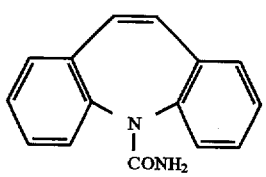

is described in U.S. Pat. No. 2,948,718. It is a medicinal substance used as an analgesic and as an anticonvulsant to prevent or relieve convulsions. When a patient is being treated with a drug, such as carbamazepine, it is important to monitor the levels of the drag in the patient's serum.

A variation of carbamazepine, the dibenzazepine derivatives described in U.S. Pat. No. 3,221,011, are pharmaceutical preparations for administration enterally or parentally. They have the general structure

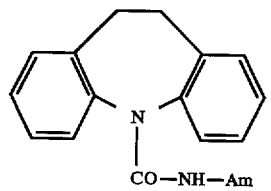

where Am may signify the radical —$NH_2$ a monomethyl, monoethyl, mono-n-propyl, mono-isopropyl, mono-n-butyl, mono-isobutyl or mono-tert-butylamino radical, a dimethyl, diethyl, di-n-propyl, diisopropyl, di-n-butyl, diisobutylamino radical, a methylethylamino, methyl-n-propylamino, methylisopropylamino or ethylisopropylamino radical.

Particle reagents have been used as carriers for hapten, proteins or other compounds of biological interest in assays for the quantitative detection of bacteria, cell surface antigens, serum proteins or other analytes to provide increased sensitivity to visual or instrumental detection of agglutination reactions. Particle reagents having a polymer inner core with a high refractive index and a polymer outer shell with epoxide functional groups covalently bound, directly or indirectly, to compounds of biological interest for use in sensitive light scattering immunoassays are described in U.S. Pat. Nos. 4,401,765 and 4,480,042. The patents described the preparation of reagents for measuring the concentration of certain specific drugs e.g., gentamicin, theophylline and digoxin, in serum. There is no example of a polymer particle reagent specific to carbamazepine. The carbamazepine structure shown above, with its single amino group, will not bind to the epoxy functional group on the polymer outer shell. The dibenzazepine derivative described in U.S. Pat. No. 3,221,011 is a 10,11 dihydro dibenzazepine derivative and is not a carbamazepine. Therefore, it would not be useful in the preparation of carbamazepine antigens for the detection and measurement of carbamazepine levels in serum.

U.S. Pat. No. 4,058,511 describes antigens and antibodies of the formula.

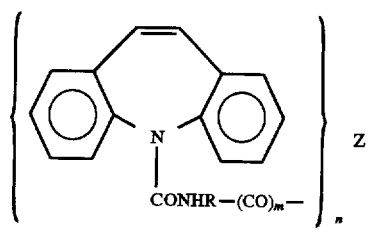

where R is a linking group of from 0 to 8 carbon atoms and 0 to 1 heteroatom, there being at least two carbon atoms between heteroatoms in the chain. The compound of this patent attaches to proteins or haptens via the carbonyl group. It would not be a suitable candidate for attachment to the electrophilic epoxide polymer particles of U.S. Pat. Nos. 4,401,765 and 4,480,042 because it has no available nucleophilic moieties.

It is an object of the present invention to provide a new carbamazepine compound for covalent attachment to a particle for use in immunoassays for monitoring carbamazepine in a patient's serum. It is a further object of the present invention to provide a carbarnazepine immunogen for the production of carbarnazepine antibodies for use in competitive immunoassays and other immunoassays for the detection of carbamazepine in patient serum. Finally, it is an object of the present invention to provide a method of making the novel carbamazepine compounds.

SUMMARY OF THE INVENTION

The objects of the present invention are achieved by a novel carbamazepine hydrazide compound suitable for covalent attachment to a particle reagent, or to proteinaceous materials, having the general formula

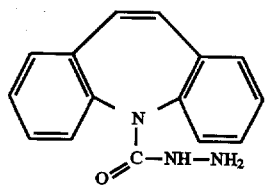

The present invention also provides a novel carbamazepine acid compound suitable for attachment to proteins for the production of carbamazepine immunogens. The carbamazepine antigen of the present invention has the following general structure:

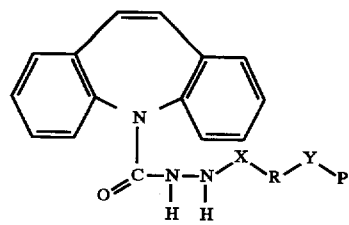

where X is C=O, $CH_2$ or $SO_2$; Y is C=O, $CH_2$, $SO_2$; R is an alkyl and P is a protein or a hapten.

The invention also includes a method which may be used to make a carbamazepine antigen. The method includes generally the steps of (i) reacting triphosgene with iminostilbene in a substantially oxygen free environment, (ii)

adding hydrazinc monohydrate and refluxing in a substantially oxygen free environment for a period of time sufficient to permit the formation of a precipitate having the structural formula of the carbamazepine hydrazide compound described above, (iii) filtering the precipitate, (iv) then reacting the preferably purified precipitate in the presence of a base with a reactant selected from the group consisting of succinic anhydride, bromoacetic acid and halogen substituted aliphatic sulfonic acid for a period of time sufficient to form a carbamazepine-acid having the structural formula

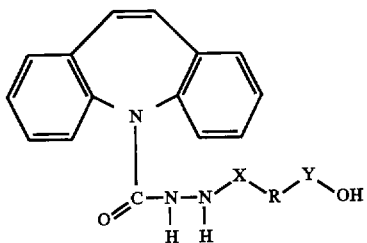

where X is selected from the group consisting of C=O, CH$_2$ and SO$_2$, Y is selected from the group consisting of C=O, CH$_2$ and SO$_2$, and R is an alkyl, (v) synthesizing a carbamazepine-NHS ester by dissolving the carbamazepine-acid and reacting the dissolved carbamazepine-acid with disuccinimidyl carbonate in the presence of a base, and, (vi) reacting the carbamazepine-NHS ester with an aqueous buffered solution of a protein. Alternatively, instead of reacting the dissolved the carbamazepine-acid with disuccinimyyl carbonate and the step subsequent thereto,(v)–(vi), the method may proceed by the alternate steps of (v) dissolving a mixture of carbamazepine-acid and hydroxybenzotriazole hydrate in a solvent, (vi) combining the mixture with dicyclohexyl carbodiimide to produce an activated carbamazepine-oxybenzotriazole acid, and (vii) reacting the activated carbamazepine-oxybenzotriazole acid with a solution of a protein.

The present invention further includes a carbamazepine particle reagent and a method for using the reagent in an immunoassay.

DESCRIPTION OF THE PREFERRED EMBODIMENTS

The novel carbamazepine hydrazide compound of the present invention provides an excellent nucleophilic carbamazepine for covalent attachment to an electrophilic polymer particle which was not heretofore available. Any electrophilic particle reagent may covalently attach to the nucleophilic carbamazepine compound of the present invention. A preferred particle reagent is a polymer particle, and most preferably a polymer particle having an inner core and an outer shell, wherein the inner core is a polymer having a refractive index of not less than 1.54 as measured at the wavelength of the sodium D line and the outer shell is a polymer of an ethylenically unsaturated monomer having a functional group capable of reacting with a complementary functional group on a compound of biological interest, such as the carbamazepine hydrazide compound of the present invention. The functional groups of the polymer particle outer shell polymer in general can be, for example, epoxy, carboxyl, amino, hydroxyl and aldehyde. For purposes of illustrating the preferred embodiment of this invention only and not for the purpose of limiting the scope of particle reagents to which the carbamazepine compound of this invention may be attached, the functional group used to describe the invention will be the epoxy functional group. In addition to the functional group of interest, for example, epoxy functional groups, the polymer surface or outer shell can further include other ethylenically unsaturated monomers in an amount sufficient to produce water insoluble polymer particles where that characteristic is desired. The outer shell may be a homopolymer. It may be formed by polymerization in the presence of the inner core and, if not a homopolymer, should not include more than 10, and preferably, not more than 5, parts by weight of the monomers of the inner core. The preferred polymer particle with which the invention is used may have an approximate diameter in the range of 0.03–0.1 µm.

The particle reagent is covalently attached, directly or through a proteinaceous material, to a compound of biological interest or its antibody. The monomers which can be used in the preparation of the polymer particle and the method of preparation are set forth in U.S Pat. Nos. 4,401,765 and 4,480,042, the specifications of which are incorporated herein by reference. The preferred monomers for particles having epoxy functional groups include glycidyl methacrylate, glycidyl acrylate, vinyl glycidyl ether, and methallyl glycidyl ether.

The synthesis of the nucleophilic carbamazepine hydrazide and of carbamazepine-acid (CBMP-acid) and its immunogens proceed generally as follows:

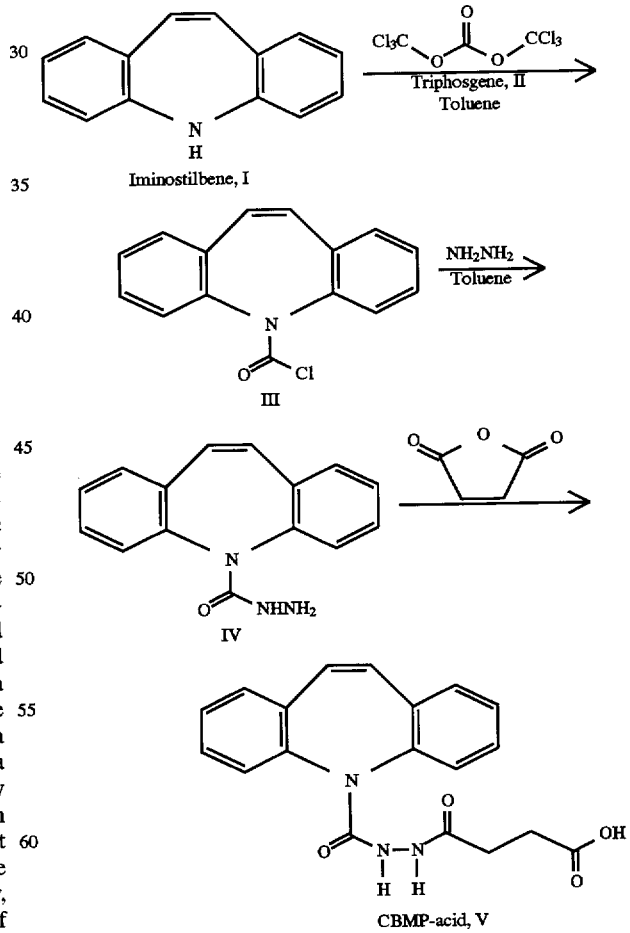

The reagents used in Examples 1 and 2 are set forth in Table I below.

TABLE I

|  | Formula Weight (FW) | W (g) | mol |
|---|---|---|---|
| Iminostilbene, I | 193.25 | 0.9650 | 0.005 |
| Triphosgene, II | 296.74 | 0.5441 | 0.00183 |
| Hydrazine hydrate | 50.06 | 0.7509 | 0.015 |
| Toluene (solvent) |  | 30 mL |  |
| Succinic Anhydride | 100.07 | 1.00 | 0.01 |
| Triethyl amine (TEA) (base) | 101 | 1.50 | 0.015 |

EXAMPLE 1

Triphosgene Reacted with Iminostilbene

1) Into a 100 mL three-neck flask equipped with a reflux condenser, an additional funnel and a nitrogen inlet, was added 0.9650 g (0.0050 mol) of compound I (iminostilbene), 0.5441 g (0.00183 mol) of compound II (triphosgene) and 30 mL toluene, as a solvent. The mixture was stirred and refluxed under nitrogen over 2 hrs until the solution became a light yellow-color. If the color does not change after 2 hr refluxing, 40 mg more triphosgene should be added, and refluxed one more hour. The solution, which contains compound III, is cooled to room temperature.

2) To the three neck flask containing the above solution, was added 1.250 g hydrazine monohydrate (0.02497 mol) with stirring. Then the reaction was refluxed under nitrogen for 2 hr and stirred at room temperature for another 2 hr. Then the mixture was cooled to room temperature, yielding extensive precipitation. The precipitate was filtered to obtain a white (yellowish) solid, compound IV.

3) To purify compound IV, the solid precipitate, compound IV from step 2), was dissolved into 30 mL chloroform. The chloroform was extracted with 1 N HCl (10 mL×3). The product was in the HCl solution. The HCl solution was washed with chloroform (10 mL×3). Then 2 N sodium hydroxide solution was added to the HCl solution and the pH adjusted to 11. The basic solution was then extracted with chloroform (15 mL×3) and the chloroform solution was dried with sodium sulfate (2–3 g). The chloroform was removed by rotary evaporation and the purified product, compound IV, remained. The weight, after the product was dried under vacuum, was 0.9661 g, indicating a yield of 76.9% compound IV from iminostilbene. Compound IV, the hydrazide, carbamazepine with an additional amine functionality, may be covalently bound to a polymer particle, such as the particles described above and in U.S. Pat. Nos. 4,401,765 and 4,480,042, bound to proteinaceous materials, such as proteins or haptens, or further processed to form the carbamazepine-acid, compound V above. Example 12 demonstrates the preparation of the carbamazepine particle reagent.

EXAMPLE 2

Carbamazepine-acid production by Reacting Compound IV with Succinic Anhydride 1) 0.5 g (0.0019897 mol) of compound IV and 0.404 g (0.0040 mol) triethyl amine were dissolved into 30 mL THF. A solution Of 0.1990 g succinic anhydride (0.001990 mol) with 10 mL THF was added into the compound IV solution with stirring. The mixture was stirred at room temperature over 10 hrs. The reaction was monitored with thin liquid chromatography (TLC) until compound IV was gone, using silica gel TLC and 85% EtOAc/15% EtOH solvent. The R$_f$ of compound IV and CBMP-acid, compound V, were 0.5–0.6 and 0–0.1, respectively.

2) THF was removed by rotary evaporation and the residues were dissolved into 30 mL chloroform. The product, carbamazepine acid, was extracted from the solution with 0.1 N sodium hydroxide (10 mL×3). The NaOH solution was then washed With chloroform (10 mL×3). The NaOH solution was acidified with 1 N HCl until the pH reached 2–3. The acid solution was extracted with chloroform (15 mL×3). The chloroform solution was then dried with sodium sulfate (2–3 g). The solvent was removed by rotary evaporation to afford the product, CBMP-acid. The percent yield from compound IV to CBMP-acid was determined by weighing the product, after drying under vacuum, and comparing that weight to the weight of compound IV added above.

If the succinic anhydride is replaced with another linker, the X and Y constituents can be altered. For example, to produce CBMP-acid where X is $CH_2$ and Y is $C=O$, the succinic anhydride in step 1 of Example 2 is substituted with bromoacetic acid, $BrCH_2COOH$.

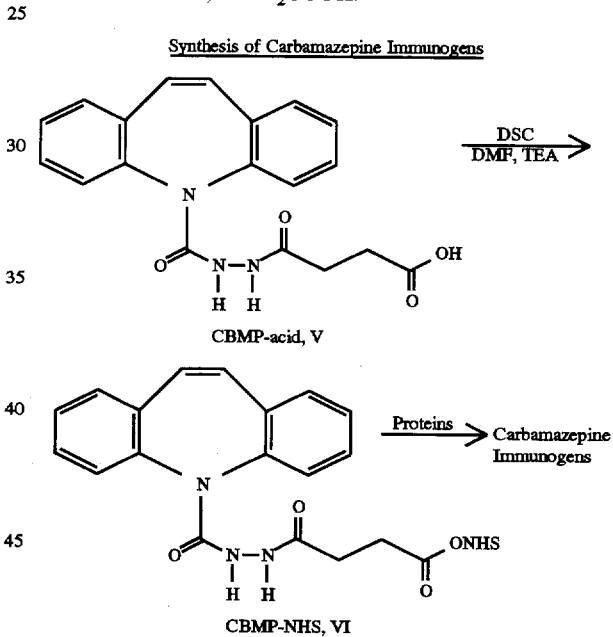

Synthesis of Carbamazepine Immunogens

The reagents used in Examples 3–7 are set forth in Table II below.

TABLE II

|  | Formula Weight (FW) | W (g) | mol |
|---|---|---|---|
| CBMP-acid, V | 351.3 | 1.93 | 0.01 |
| Disuccinimidyl Carbonate (DSC) | 256.2 | 2.97 | 0.01 |
| Triethyl amine (TEA) | 50.06 | 1.50 | 0.03 |
| DMF (Solvent) |  |  |  |
| KLH, Keyhole Limpet Hemocyanin |  |  |  |
| PSG, Pumpkin Seed Globulin |  |  |  |
| Ovalbumin |  |  |  |

EXAMPLE 3

Synthesis of CBMP-NHS ester, Compound VI

1) A stock solution of DSC was prepared as follows: 213.08 mg of DSC was weighed into a 8 mL vial. To that was added 5,281 mg DMF. The mixture was agitated until the DSC dissolved. The density of the solution was determined by weighing a 1000 μL aliquot. A typical density is d=0.97458 mg/μL. The DSC concentration is calculated from the following equation:

$C_{DSC}$ = {[Wt. of DSC] ×

[Density of Solution]}/{[$MW$ of DSC] × [Wt. of Solution]} =

[213.08 mg × 0.97458 mg/μL]/[256.2 × 5494.08 mg] =

1.475 × $10^4$ mmoles/μL 2) 75.0 mg (0.2135 mmole) CBMP-acid was weighed into a 6 mL vial. A magnetic stirrer bar was added. 1450 μL dry DMF was pipetted to dissolve the CBMP-acid. 1592.2 μL of the DSC stock solution from step 1 and 75 μL dry triethyl amine were pipetted into the above solution. The mixture was stirred for one hour at room temperature in the dark to produce compound VI, the CBMP-NHS ester. If a stock solution is not needed, for example for batch processing, the amounts of the reagents set forth in Table II are used in step 1).

Synthesis of CBM-protein Immunogens

EXAMPLE 4

Keyhole Limpet Hemocyanin buffer solution

1) Keyhole Limpet Hemocyanin (KLH) in water. 150 mg of KLH (available from Sigma Corp.) was dissolved in 24 mL deionized water in a 40 mL centrifuge tube by stirring gently overnight in a cold room, at 4° C. The tube was centrifuged and the supernatant solution poured into a 1-oz, screw-capped bottle (to be used as reaction vessel for the conjugate synthesis), then stored in the refrigerator.

2) 4-ethylmorpholine (4-EM) buffer concentrate (1.25 M). 6.25 mL of 1.00N HCl was pipetted into a 10 mL volumetric flask. The flask was cooled in ice and 591 μL of 4-EM was added carefully because of the resulting heat evolution. After the addition was complete, the contents of the flask were allowed to come to room temperature. The solution was diluted to exactly 10.00 mL with water and mixed thoroughly.

3) KLH in 50 mmolar 4-EM buffer. Immediately before it was used, the KLH/water solution was removed from the refrigerator and a magnetic stirrer bar was added. The solution was stirred briskly and 1000 μL of the 4-EM concentrate of step 2) was added before proceeding with the conjugate synthesis.

EXAMPLE 5

Pumpkin Seed Globulin (PSG) in 4 M NaCl/0.15 M NaHCO₃

1) 4 M NaCl/0.15 M NaHCO₃. 23.40 g of sodium chloride and 1.26 g of sodium bicarbonate were weighed into a 100 mL volumetric flask, then dissolved with deionized water to exactly 100.0 mL.

2) PSG in 4 M NaCl/0.15 M NaHCO₃. 150 mg of pumpkin seed globulin was dissolved in 25 mL of 4 M sodium chloride/0.15 M sodium bicarbonate solution into a 1-oz, screw-capped bottle with a magnetic stirrer bar. The solution was stirred before proceeding with the conjugate synthesis.

EXAMPLE 6

Ovalbumin in 0.15 M NaHCO₃

1) 0.15 M NaHCO₃. 1.26 g of sodium bicarbonate was weighed and added into a 100 mL volumetric flask, then dissolved with deionized water to exactly 100.0 mL.

2) Ovalbumin in 0.15 m NaHCO₃. 150 mg of ovalbumin (available from Sigma Corp.) was dissolved in 25 mL of 0.15 M sodium bicarbonate into a 1-oz, screw-capped bottle with a magnetic stirrer bar. The solution was stirred before proceeding with a conjugate synthesis.

EXAMPLE 7

Conjugation of CBMP-acid to Proteins 1) 1020.0 μL of the CBMP-NHS DMF solution of Example 3 was pipetted into each of the protein buffer solutions of Examples 4, 5 and 6, with stirring. The reaction was stirred for 10 min., then stored in a cold room at 4° C. overnight. If the solutions appeared to be cloudy, they were agitated gently.

2) Each solution was dialyzed against three changes of deionized water, then against three changes of phosphate buffered saline (PBS) buffer.

The concentration of each protein-carbamazepine conjugate solution was calculated according to the weight of the protein in mg divided by the total volume of the solution in mL.

The carbamazepine immunogens can be synthesized by the alternative procedure shown below. The procedure shown below is preferred because the yield has been estimated to be much higher than the yield obtainable from the procedure of Examples 3 and 7. When the CBMP-acid is coupled to protein using DSC/DMF as in Examples 3 and 7, the yield is lower because a greater degree of intramolecular cyclization occurs. Cyclized products are inactive, and, therefore, not suitable as immunogens. To detect the levels of cyclization, the TLC procedure described above is used.

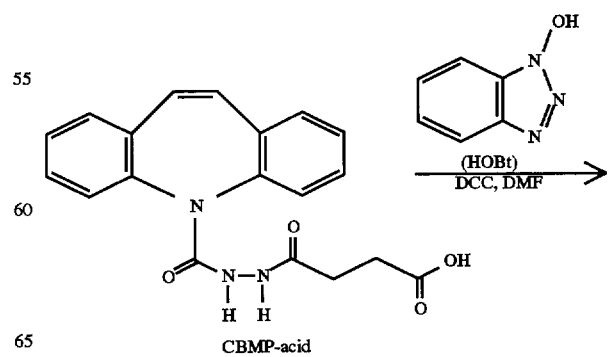

CBMP-acid

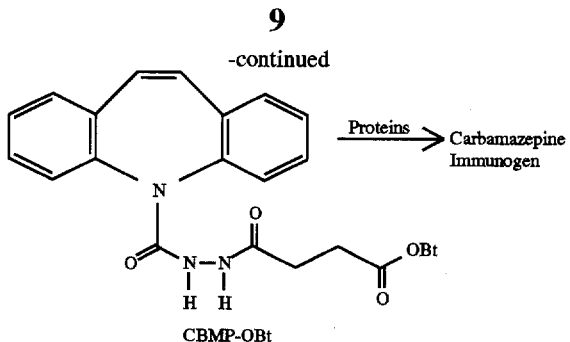

CBMP-OBt

The reagents used in Examples 8–10 are set forth in the Table III below.

TABLE III

|  | FW | W (g) | mmol |
|---|---|---|---|
| CBMP-acid, V | 351.3 | 23.71 | 0.0675 |
| Dicyclohexyl carbodiimide (DCC) | 206 | 13.91 | 0.0675 |
| Hydroxybenzotriazole hydrate (HOBt) | 153.14 | 12.41 | 0.0810 |
| DMF (Solvent) |  | 300 μL |  |
| KLH |  | 50 mg |  |
| Ovalbumin | 45,163 | 50 mg | 0.00111 |

EXAMPLE 8

Synthesis of CBMP-OBt ester

Synthesis of CBMP-OBt ester 1) 23.71 mg (0.0675 mmole) CBMP-acid and 12.41 mg (0.0810 mmole) HOBt were weighed into a 2 mL vial. A magnetic stirrer bar was added. 300 μL dry DMF was pipetted into the vial to dissolve CBMP-acid and HOBt.

2) 13.91 mg (0.0675 mmole) of DCC was weighed and added into the solution of step 1) with stirring.

3) The reaction was stirred at room temperature for two hr. The activated acid was now ready to couple with proteins.

Synthesis of CBMP-protein Immunogens

EXAMPLE 9

Ovalbumin in 0.15 M NaHCO₃

1) 0.15 M NaHCO₃. 0.315 g of sodium bicarbonate was weighed and added into a 25.0 mL volumetric flask. It was dissolved with deionized water to exactly 25.0 mL.

2) Ovalbumin in 0.15 M NaHCO₃. 50 mg of ovalbumin was dissolved in 8 mL of 0.15 M sodium bicarbonate into a 16 mL screw capped vial with a magnetic stirrer bar.

EXAMPLE 10

KLH water solution

1) KLH in water. 50 mg of KLH was dissolved in 8 mL deionized water in a 16 mL centrifuge tube by stirring gently overnight in the cold room at 4° C. The solution was centrifuged and the supernatant was poured into a 16 mL screw capped bottle (to be used as reaction vessel for the conjugate synthesis) then (stored in the refrigerator.

EXAMPLE 11

Conjunction of CBMP-acid to Proteins 1) 100 μL of the CBMP-OBt DMF solution (0.0225 mmole of CBMP-OBt) was pipetted into each of the KLH water and ovalbumin buffer solution of Examples 9 and 10 with stirring. The reactions were stirred gently at room temperature for 10 min., then stored in a cold room at 4° C., overnight.

2)* Each solution was dialyzed against three changes of deionized water, then against three changes of PBS buffer (using dialysis tubing with a 6–8,000 MW cut-off range).

* gel filtration can be used to remove small molecules in this stage.

Each protein-carbamazepine conjugate solution of Example 11 was weighed. The concentration of the protein-carbamazepine conjugates, in mg/mL, was calculated using the formula C=(Wp×0.85)/V, where Wp is the weight of the protein in mg and V is the total volume of the solution in mL, assuming that 1 g solution weight equals 1 mL solution volume. Thus, for ovalbumin, C=(50mg×0.85)/V, and for KLH, C=(50mg×0.85)/V.

The method of preparing the polymer reagent to which the product compound IV, of Example 1 is covalently attached is set forth in U.S. Pat. Nos. 4,480,042 and 4,401,765.

EXAMPLE 12

Preparation of Carbamazepine Particle Reagent and its Use 50 mg of the carbamazepine hydrazide, compound IV, prepared in Example 1 in 5 mL of deionized water is neutralized by adding barium hydroxide until no further precipitate is formed. The precipitate is removed by centrifugation. The supernatant is added to a mixture of 5 mL of the polystyrene/polyglycidyl methacrylate polymer particle prepared as in U.S. Pat. No. 4,401,765 and 5 mL of a 0.1% suspension of "Schercozoline" S (a substituted imidazoline from stearic acid, available from Sober Chemical Co.) at a pH of 8.5 adjusted with potassium hydroxide. The mixture is warmed to 75° C. for approximately 30 min, diluted with 200 mL of water, and deionized using a mixed bed ion exchange resin. 0.4 mL of the resulting particle reagent is added to 20 mL of 0.1% sodium dodecyl sulfate (SDS) followed by the addition of 0.2 mL of 0.020 M phosphate buffer (pH 7.43) containing 0.3 m NaCl and 0.1% SDS.

This mixture is tested for immunological reactivity by well known techniques, for example, by adding, separately, human serum, carbamazepine, anti-carbamazepine (prepared as in Example 13), and an agglutinating agent prepared from a mixture of anti-carbamazepine and carbamazepine and by measuring the rate of change in turbidity. Agglutinating agents are added in agglutination inhibition reactions. The agglutinating agent can be an antibody to the carbamazepine or its analog or a particle reagent based on a polymer particle as described herein, covalently attached to an antibody to carbamazepine or its analog. Analog or antigen analog of a carbamazepine compound as used herein means any substance or group of substances which share antigenic determinates and, therefore, behave substantially the same as carbamazepine with respect to binding specificity for the antibody to carbamazepine.

EXAMPLE 13

Preparation of Carbamazepine Immunogens

Each of the carbamazepine-protein conjugates prepared as in Examples 7 and 11 are separately injected into mice for production, by means of normal immunologic responses, of mouse anti-carbamazepine antibody according to well known techniques. Hybridomas may be formed from fused myeloma cells and the normal spleen cells of the immunized mouse by well known techniques. The antibodies thus produced are then screened in vitro by well known techniques for monoclonal mouse anti-carbamazepine antibodies. The mouse anti-carbamazepine antibodies are purified by known techniques and available for use as the antibody in immunoassays, such as the light scattering immunoassays, for measurement of carbamazepine in serum samples as described above.

The particle reagent of Example 12 can be suspended in a substantially aqueous medium which can further contain buffer, serum components and surfactants to yield a monodisperse particle reagent for use in light scattering immunoassays. Depending on the sensitivity required, the reagents may be used in a direct particle enhanced turbidimetric immunoprecipitation technique, or in direct, competitive or inhibition assays. The carbamazepine reagent may be used in commercially available automated clinical chemistry analyzers, such as the aca™ discrete clinical analyzer or the Dimension™ chemical analyzer (available from E. I. du Pont de Nemours and Company), to measure carbamazepine levels in human serum.

In the aca™ analyzer, an aliquot of serum (0.20 mL) containing an unknown mount of carbamazepine, would be added to an amount of 0.15 M phosphate buffer, pH 7.8 (4.98 mL), containing 2.5% polyethylene glycol 6000. Anti-carbamazepine (0.004 mL) prepared as in Example 13 would be added and allowed to incubate for about 3.5 min. The reaction is initiated by the addition of 0.150 mL carbamazepine particle reagent prepared as in Example 12. The increase in turbidity, due to particle aggregation, is measured in the aca™ analyzer as the difference in the absorbance at 340 nm (rate of change) 29 s and 46 s after particle addition.

What we claim is:

1. A compound having the structural formula

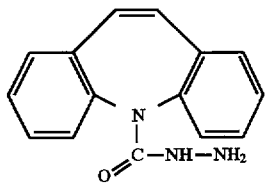

* * * * *

UNITED STATES PATENT AND TRADEMARK OFFICE
CERTIFICATE OF CORRECTION

PATENT NO.   : 5,688,944
DATED        : November 18, 1997
INVENTOR(S)  : Chengrong Wang It is certified that error appears in the above-identified patent and that said Letters Patent is hereby corrected as shown below:

Column 1, Line 25: Delete "drag" and insert --drug--.

Column 2, Line 26: Delete "carbarnazepine" and insert --carbamazepine--

Column 5, Line 64: Delete "Of" and insert --of--.

Column 6, Line 10: Delete "With" and insert --with--.

Column 10, Line 35: Delete "Sober" and insert --Scher--.

Column 11, Line 25: Delete "mount" and insert --amount--.

Signed and Sealed this

Twenty-seventh Day of October, 1998

Attest:

BRUCE LEHMAN

*Attesting Officer*       *Commissioner of Patents and Trademarks*